United States Patent
Brady et al.

[19]

[11] Patent Number: 6,066,296
[45] Date of Patent: *May 23, 2000

[54] SAMPLE ADDITION, REAGENT APPLICATION, AND TESTING CHAMBER

[75] Inventors: Terry E. Brady, Gladstone; Michael F. Corsello, West Milford, both of N.J.

[73] Assignee: Array Medical, Inc., Somerville, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/935,985

[22] Filed: Sep. 23, 1997

[51] Int. Cl.⁷ ..................................................... G01N 33/48
[52] U.S. Cl. ........................... 422/63; 422/61; 422/82.05
[58] Field of Search ................. 422/56, 58, 61, 422/63, 64, 82.05

[56] References Cited

U.S. PATENT DOCUMENTS

| | | |
|---|---|---|
| 3,241,432 | 3/1966 | Skeggs et al. . |
| 3,595,079 | 7/1971 | Grahn ........................................ 73/204 |
| 3,678,151 | 7/1972 | Horonick et al. . |
| 3,779,383 | 12/1973 | Ayres . |
| 3,837,376 | 9/1974 | Brown et al. . |
| 3,871,099 | 3/1975 | Kahn . |
| 3,950,134 | 4/1976 | Miles ......................................... 422/71 |
| 3,992,150 | 11/1976 | Retzer . |
| 4,104,025 | 8/1978 | Retzer . |
| 4,348,207 | 9/1982 | Cappel . |
| 4,449,539 | 5/1984 | Sarstedt . |
| 4,664,274 | 5/1987 | Konrad . |
| 4,853,336 | 8/1989 | Saros et al. . |
| 5,163,442 | 11/1992 | Ono ........................................... 128/760 |
| 5,168,067 | 12/1992 | Miller et al. . |
| 5,297,561 | 3/1994 | Hulon . |
| 5,632,399 | 5/1997 | Palmieri et al. ........................ 220/253 |

*Primary Examiner*—Lyle A. Alexander
*Attorney, Agent, or Firm*—Gibbons, Del Deo, Dolan, Griffinger & Vecchione

[57] ABSTRACT

The present invention utilizes a novel reaction chamber. The reaction chamber is made from a pierceable self-sealing material which may be in the form of a long, narrow tube. The may contains a single reagent within the entire length of the tube or the tube may be segmented into a plurality of distinct chambers. Numerous tests can be performed within a given tube, separated either by distance or a physical barrier, with no degradation or interference between the testing sites. The test results may be conveniently determined using any of the known detection methodologies, including photometric, electromechanical, spectrophotometric, and nephlometric detection mechanisms.

8 Claims, 3 Drawing Sheets

SAMPLE ADDITION, REAGENT APPLICATION, AND TESTING CHAMBER

BACKGROUND OF THE INVENTION

Many diagnostic analyzers are designed according to one of two distinct formats. The first uses unitized testing chambers, with specific test reagents pre-loaded into each individual chamber, and sometimes utilizes whole blood as the testing sample. This type of instrument is commonly used in a point-of-care setting near the patient. Such pre-loaded, unitized systems are typically more complicated and expensive than batch analyzers. The second instrument format is exemplified by large, batch type instruments. These instruments usually employ large discrete reagent bottles from which reagents are aliquoted into a test chamber along with the patient sample at the time of the test. This type of system is usually used in a high throughput laboratory diagnostic setting.

Both instrument formats have inherent qualities and weaknesses. Unitized point of care systems are usually easy to use, do not require reagent or sample preparation, and utilize a portable platform for use at any patient location. The obvious weakness of this type of system is the limited test menu, less rigorous adherence to laboratory guidelines and test methodologies, and high cost of disposables. Alternatively, high volume random access instruments can process many samples and assess many analyses quickly, and may be used to analyze different kinds of samples such as whole blood, plasma, or serum. Unfortunately, these machines are not simple to maintain, are large and expensive, therefore centrally located, and only have economy when processing large quantities of batched samples.

Thus, there is a need for a simple, inexpensive diagnostic system which provides for a broad range of tests performable on a variety of samples in a point-of-care setting.

SUMMARY OF THE INVENTION

The present invention utilizes a novel reaction and reagent chamber. The reaction and reagent chamber is made from a pierceable self-sealing material which may be in the form of a long, narrow tube. In one embodiment, the tube contains a single reagent within the entire length of the testing tubule. This single analyte version is especially useful in assays such as home prothrombin and glucose testing in which multiple reagents or specimen convolutions are not necessary. To accommodate this single reagent version, no tubule segmentation is necessary. Each test is simply segregated by distance. Numerous tests can be performed with each tube in this format with no degradation or interference between the testing sites. The test results may be conveniently determined using any of the known detection methodologies, including photometric, electromechanical, spectrophotometric, and nephlometric detection mechanisms.

In another embodiment, the tube is segmented into discrete chambers or receptacles. Each segment of the tube contains no reagent or any desired reagent or reagents or may contain separator filters, and quality control or cleaning liquids. In similar fashion to a point of care unitized instrument, the sample to be tested may be added to a testing chamber with reagents already preloaded into it. A sample may also be loaded into an empty chamber placed among the segments for the purpose of holding an unreacted sample. The invention also allows for multiple step assays by enabling the addition of components from one segment to components contained in other segments.

Another unique feature of the invention is the ability to utilize different components of a sample to be tested. For example, whole blood may be used as the sample, or a blood sample may be filtered to ultimately test a plasma or serum sample.

DETAILED DESCRIPTION OF THE INVENTION

Figure 1:
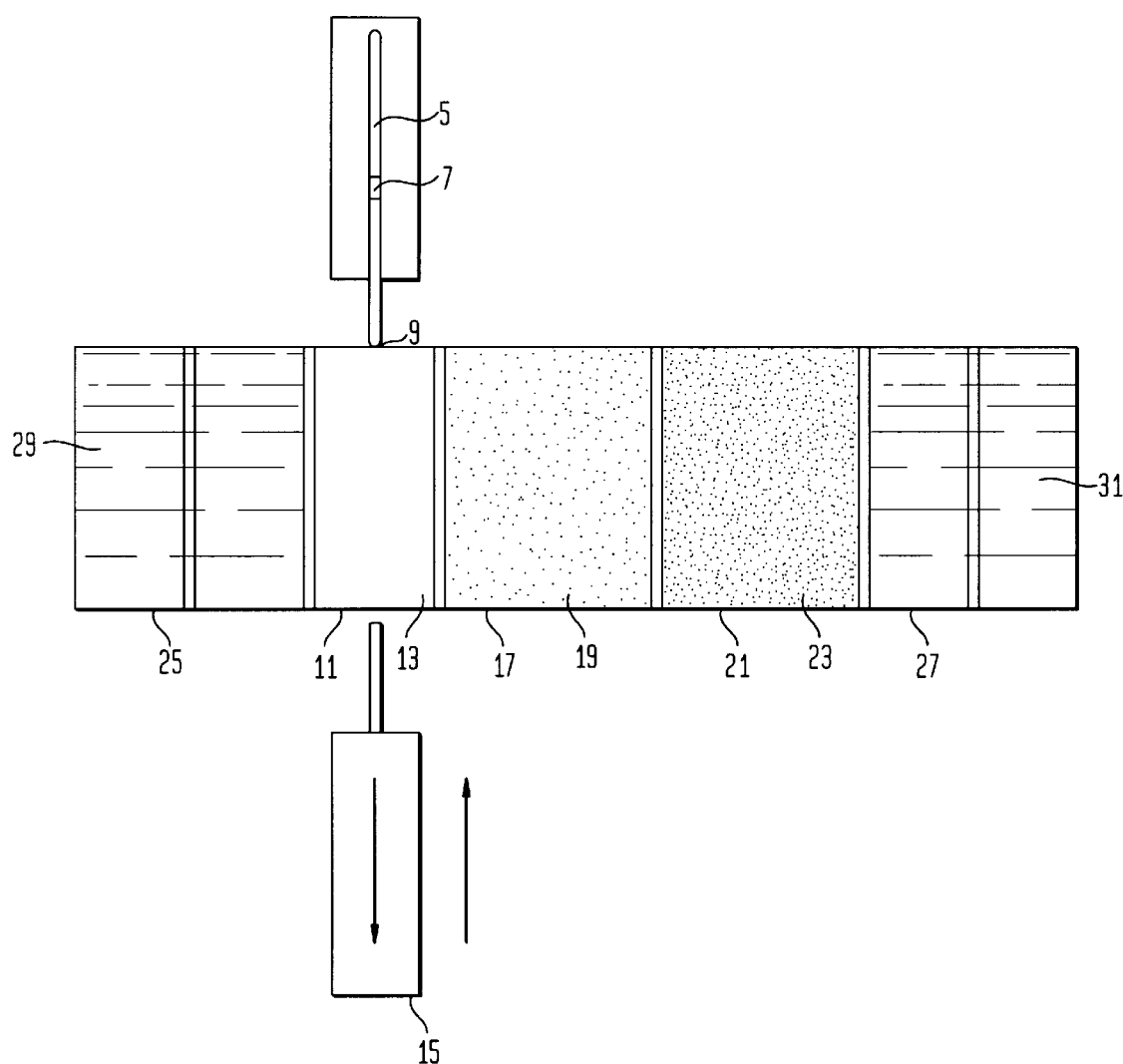
FIG. 1. shows an inventive tubing arrangement suitable for individual small scale testing FIG. 2. shows an inventive tubing arrangement suitable for multiple testing on large scale.

The present invention is based upon the use of a transparent pierceable material with self-sealing characteristics as a receptacle for holding an unreacted sample or a receptacle or crucible to contain one or more reagents and f unction as a reaction vessel. Such a material is capable of being penetrated by a small diameter object such as a syringe needle, cannula, capillary tube or other similar device, and upon the withdrawal of the syringe or other device, the opening in the material created by the piercing object closes up due to the inherent resilience of the material. The remaining perforation seals itself so that the material remains impermeable to the reagents contained therein at or near ambient pressure.

In the present invention, a material having the described characteristics of piercability and self-sealing is used to contain unreacted samples, cleansing fluids or one or more of various reagents used to conduct one or more diagnostic tests. The material may be formed into any suitable shape which will provide a chamber or space in which samples, cleaning fluids or reagents may be retained. In one embodiment of the invention, tubing of a suitable material is used to contain reagents. An example of tubing which is suitable for use to contain diagnostic reagents is Tygon™. The appropriate cross-sectional shape, diameter and length of tubing may be easily selected according to the particular requirements of any diagnostic test. The use of tubing to contain reagents and act as a reaction chamber enables the performance of any desired number of reactions in a single tube simply by selecting an appropriate length of tubing. The tubing is pierced at numerous points along the tubing to deliver a sample to be tested into the lumen of the tube to contact the appropriate reagent, where a reaction may take place between an analyte in the sample and the reagent. Thus, numerous reactions such as diagnostic tests, may be performed at various points along a single length of the tubing. Upon completion of the reaction, the reaction product may then be observed or detected inside the tube to determine the nature of any reaction which may have occurred at the point of delivery of the sample. In one embodiment of the invention, a continuous length of tubing is filled with a single reagent. The spacing interval of the points at which the tubing is pierced may be readily selected so that the distance between piercing points exceeds the distance which can be traversed by the reaction product of a single sample. In this way, numerous tests may be spatially segregated along a single length of tubing. This embodiment enables numerous performances of single types of tests utilizing the same reagent.

An example of a diagnostic test which may be conducted with a continuous length of tubing containing a single reagent is a prothrombin time test. In this example, tubing is filled with thromboplastin. Plasma samples from numerous patients are then applied by a syringe at distinct points along the tubing. Alternatively, a single patient may conduct numerous tests over time simply by applying each successive sample to a different distinct point along the tubing.

In another embodiment, the tubing may be divided into segments or separate closed compartments, by any means to accomplish such separation such as crimping the tube or providing barriers at intervals along the inside of the tubing. Each individual chamber in the segmented tube may contain a reagent. Any combination of samples, cleansing fluid and reagents may be placed in any sequence along the length of the tube. In this way, all of the different reagents needed for a multi-step diagnostic test may be provided in a given length of tubing. Alternatively, reagents for different diagnostic tests may be placed in separate chambers of the tubing.

In some tests, it may be useful to place a filter in one or more of the segments in order to separate a desired component from a sample for further analysis. For example, some tests are typically performed using blood plasma as a sample, requiring separation of the plasma from whole blood. Such a separation may be accomplished with the present invention by delivering whole blood into one side of a tube segment which contains an appropriate blood filter, and using vacuum pressure to draw plasma through the filter to the other side of the tube segment. Filtered plasma can then be extracted from the tube and delivered to another segment by a receipt/dispense needle for further testing.

The tubing containing reagents may be incorporated into a system with the appropriate devices for delivering a sample to, or drawing a sample from, the inside of the tube. Such devices may comprise any useful arrangement of receipt/dispense needles with syringes, capillary tubes or other devices capable of piercing the tubing and conveying a sample, in combination with any pumps or other devices for creating pressure or vacuum to deliver or extract sample through a syringe or capillary tube.

In another embodiment of the invention, tubing containing the desired reagents is installed on two spools or reels, with each end of the tubing connected to a reel. The reels are installed in a cassette case. The cassette is then oriented so that a portion of the tubing extending between the spools is exposed and presented to the syringes or capillary tubes which deliver and/or extract sample from the inside of the tubing to perform a test. Upon completion of each successive test or step in a test, the tubing is incrementally advanced from one spool to the other so that a new portion of the tubing is presented to the syringe mechanism. The syringe mechanism may be incorporated as an integral part of the cassette, or may be a separate mechanism.

In another embodiment, a plurality of tubes may be oriented in proximity to one another, preferably in parallel fashion. Each individual tube may be either a continuous length of tubing containing a single reagent, or may be a segmented tube, with each discrete segment containing a reagent. Just as different reagents necessary for an assay may be proximally arranged in discrete segments of a single tube, different reagents may also be placed in separate lengths of a plurality of tubes.

As is apparent, the use of pierceable, self-sealing tubing as a reagent receptacle and reaction chamber enables many kinds of tests to be simplified. The present invention will be adaptable for use in conducting any type of chemical reaction, including but not limited to industrial chemistry, biochemistry, clinical chemistry, immunochemistry, and medical diagnostic testing.

The present invention encompasses a variety of embodiments which will be apparent to those skilled in the art. The following examples further describe but do not limit the scope of the invention.

EXAMPLE 1

Samples may be prepared for test analysis in a variety of ways according to the desired setting. In one embodiment suitable for limited menu, low throughput testing. As shown in FIG. 1, a patient blood sample is applied directly from a finger stick or venipuncture to a tapered plastic capillary tube 5 with a blood component filter 7 located therein which allows a desired sample medium, in this case serum or plasma to pass therethrough. Based on the test desired, the proper combination of tubing segments is selected. The tapered end 9 of capillary tube 5 pierces a selected segment of the tubing, for example, sealed sample chamber 11 containing no reagent. Desired sample medium 13 passes into the selected segment 11 facilitated by a vacuum created by a receipt/dispense needle 15, as described above, which will also pierce the tubing material of the present invention at the same selected segment. If desired, after the testing medium 13 is acquired in a first selected segment 11, a measured quantity of the medium 13 may be removed from the first selected segment 11 and delivered to a second selected segment 17 by means of the receipt/dispense needle 15. The action of receipt/dispense needle 15 serves to mix the measured quantity of sample medium with first reagent 19 in second selected segment 17. As will be understood by the artisan, this process can be repeated as often as desired with any number of segments and reagents. For example, a measured quantity of the mixed first reagent 19/sample medium 13 may be removed from second selected segment 11 and delivered to third selected segment 21 containing second reagent 23. Again, the receipt/dispense needle provides mixing action. It may be desirable, when multiple piercings are to be performed to have the receipt/dispense needle clean itself between piercings. This may be accomplished by filling certain segments such as segments 25 and 27 with cleansing water or any other appropriate cleansing fluid or gel 29 and 31 so that the receipt/dispense needle cleanses itself in the process of piercing these particular cleansing segments which are selected at appropriate intervals. After testing is complete, the specimen and reagents remain safely in the used, sealed chambers.

EXAMPLE 2

Figure 2:
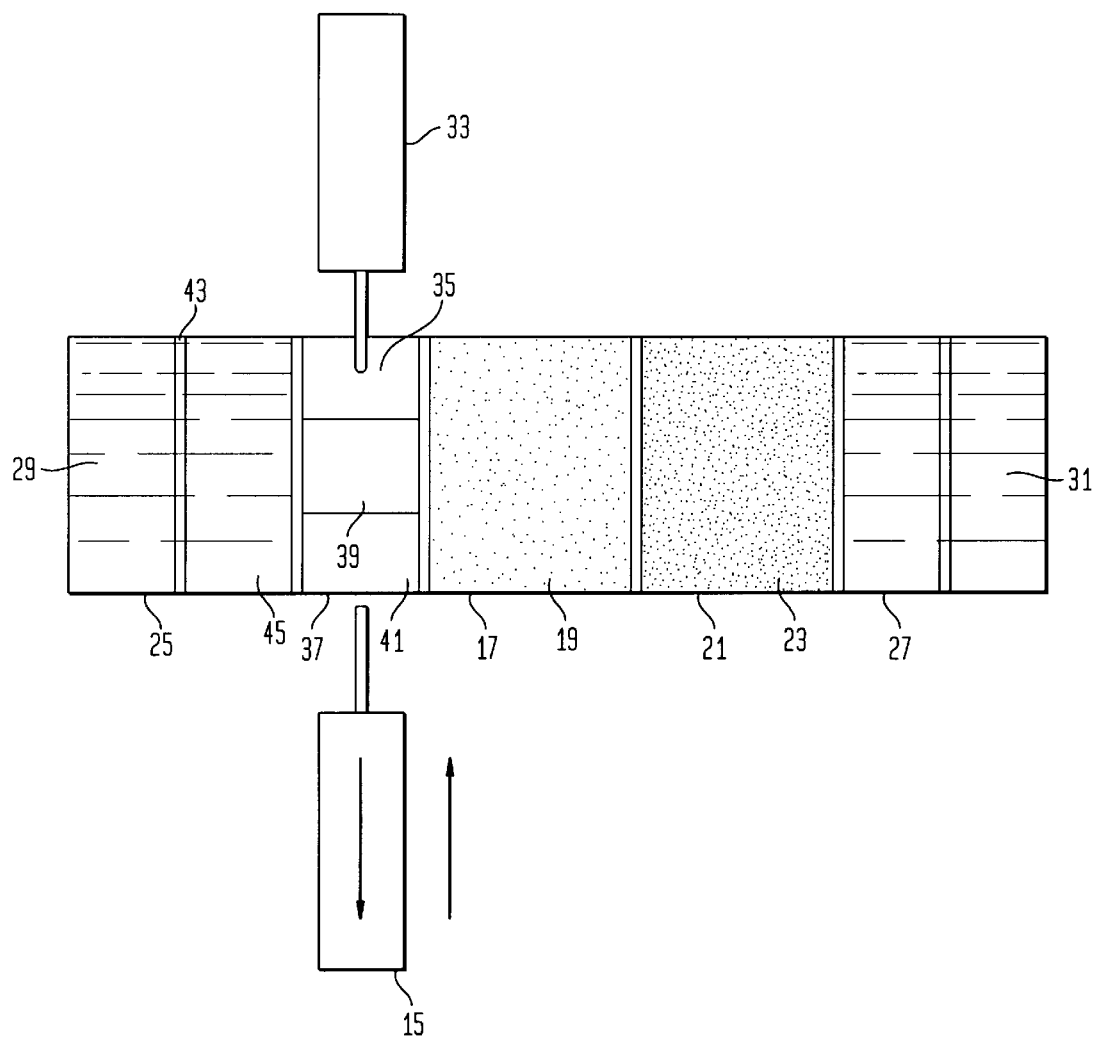

Another embodiment of the invention is designed for higher volume, larger test menu selection, and central instrument location environments. This would include hospital labs, satellite labs, central labs, outpatient labs, and physician office labs. This version of the invention is similar in design to the point of care version in parts and functionality, except for the sample delivery/filtration system. Since this analyzer receives samples from a variety of locations, into a variety of blood collection tubes, the blood component separation filter is located inside one of the tube segments. In addition, other segments also contain test re-initiators such as calcium chloride, a common laboratory reagent for coagulation studies. A diagnostic test on this system is performed as shown in FIG. 2 wherein like parts are like numbered to those in FIG. 1. Whole patient blood collection 33 tube is applied to the instrument. Based on the test selected, the proper combination of tubule segments is selected. Whole blood 35 is then transferred from collection tube 33 to the component filter segment 37 with component filter 39 located therein. The dispense/receipt needle applies a vacuum to pull the desired testing medium 41 through the filter 39. The application needle 33 begins its cleansing process preparing for the next specimen. This is accomplished by means (not shown) which permit application needle 33 to move to segment 25 containing cleansing water or other cleansing gel or fluid 29 and pierce the segment 25 for the cleansing process. Receipt/dispense needle, 15 removes desired testing medium 41 from segment 37 and dispenses a measured amount into test chamber 17 containing reagent 19. Receipt/dispense needle 15 proper testing chamber. The receipt/dispense needle mixes the sample as described previously. In a single step procedure, the test detection takes place in test chamber 17. In a two step after the proper time interval has elapsed, receipt/dispense needle 15 removes the proper test volume and applies it test chamber 21 containing reagent 23. Again, the needle provides mixing action. After application to chamber 27, receipt/dispense needle cleans itself. This may be accomplished by means (not shown) which allow receipt/dispense needle 15 to move back to segment 25 for cleaning. Segment 35 may have a barrier 43 located therein which keeps cleansing water or other cleansing fluid or gel 45 separate from cleansing fluid 29 which has been contaminated with sample from sample application needle 33 when it cleaned itself previously. As will be understood by the artisan, this process can be repeated as often as desired with any number of segments and reagents. After testing is complete, the specimen and reagents remain safely in the used, sealed chambers.

Figure 3:
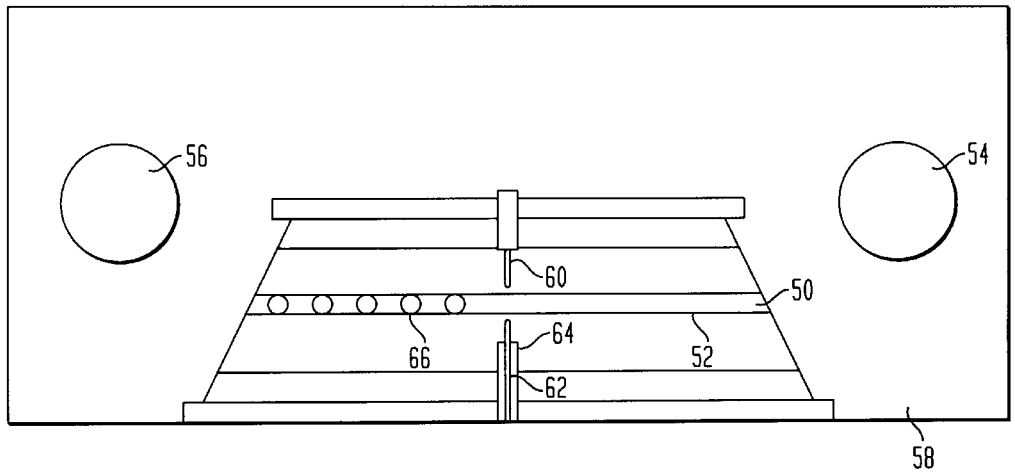
FIG. 3. shows a cassette arrangement containing unsegmented tubing filled with a single reagent.

FIG. 3 shows a cut away view of a cassette arrangement of the present invention wherein a single reagent 50 fills tubing 52. Tubing 52 is wound around spools 54, 56 within cassette 58 and is capable of advancing so that a new portion of tubing 52 containing reagent 50 is exposed to piercing by receipt/dispense needle 60 and capillary tube 62 (held in capillary tube holder 64) as the tubing advances. Tubing 52 is not segmented, rather each reaction is separated merely by space. The nature of the reactions utilizing such a non segmented tube are those which are contained in one area when they are completed such as a prothrombin time test. As a result previous tests exemplified by previous test 66 have reaction products which remain in place in tubing 52 and do not interfere with subsequent tests.

Figure 4:
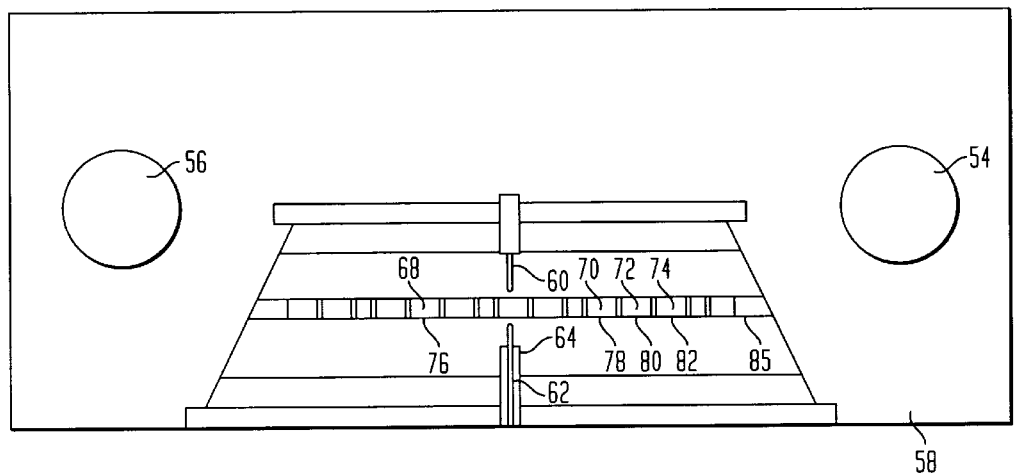
FIG. 4. shows a cassette arrangement containing segmented tubing in which the segments may contain different reagents.

FIG. 4 shows a cut away view of a cassette arrangement of the present invention utilizing segmented tubing 85. Like parts are like numbered to those in FIG. 3. In segmented tubing 85, different reagents 68, 70, 72 and 74 fill different tube segments 76, 78, 80 and 82 respectively. As the tubing advances on the spool, discrete segments are exposed to receipt/dispense needle 60 and capillary tube 62.

From the above, it should be understood that the embodiments described, in regard to the drawings, are merely exemplary and that a person skilled in the art may make variations and modifications to the shown embodiments without departing from the spirit and scope of the invention. All such variations and modifications are intended to be included within the scope of the invention as defined in the appended claims.

What is claimed is:

1. A diagnostic test device for analyzing a component in a body fluid comprising:

translucent, self-sealing tubing that can be pierced, at least one diagnostic reagent contained within said tubing, delivering means including a needle-like member extending in self-sealing relationship with said tubing for delivering said body fluid, a reaction zone within said tubing for reacting said reagent with said body fluid, analyzing means for analyzing said component wherein said analyzing means uses a light path through said tubing and a cassette housing having two rotatable spools wherein an end of said tubing is attached to one of said spools and another end of said tubing is attached to the other end of said spool.

2. The device of claim 1 wherein said detection means is photometric means.

3. The device of claim 1 wherein said detection means is a spectrophotometer.

4. The device of claim 1 wherein said translucent tubing is transparent.

5. A diagnostic test device for analyzing a component in a body fluid comprising:

translucent self-sealing tubing that can be pierced having multiple chambers, at least one diagnostic reagent contained within each of said chambers of said tubing, delivering means including a needle-like member extending in self-sealing relationship with said tubing for delivering said body fluid, a reaction zone within each of said chambers of said tubing for reacting said reagent with said body fluid, analyzing means for analyzing said component wherein said analyzing means uses a light path through said tubing and a cassette housing having two rotatable spools wherein an end of said tubing is attached to one of said spools and another end of said tubing is attached to the other end of said spool.

6. The device of claim 5 wherein said detection means is photometric means.

7. The device of claim 5 wherein said detection means is a spectrophotometer.

8. The device of claim 5 wherein said translucent tubing is transparent.

* * * * *